(12) United States Patent
Tien et al.

(10) Patent No.: US 10,179,399 B2
(45) Date of Patent: Jan. 15, 2019

(54) PORTABLE POWER TOOL

(71) Applicant: Industrial Technology Research Institute, Hsin-Chu (TW)

(72) Inventors: Chun-Hsien Tien, Nantou County (TW); Chan-Ru Chang, New Taipei (TW); Chun-Wen Tang, Taoyuan (TW)

(73) Assignee: INDUSTRIAL TECHNOLOGY RESEARCH INSTITUTE, Hsin-Chu (TW)

(*) Notice: Subject to any disclaimer, the term of this patent is extended or adjusted under 35 U.S.C. 154(b) by 455 days.

(21) Appl. No.: 14/976,093

(22) Filed: Dec. 21, 2015

(65) Prior Publication Data

US 2017/0113338 A1    Apr. 27, 2017

(30) Foreign Application Priority Data

Oct. 27, 2015  (TW) .............................. 104135254 A

(51) Int. Cl.
*B25B 27/00* (2006.01)
*B25F 1/00* (2006.01)
*B25B 21/00* (2006.01)
*F04F 13/00* (2009.01)
*G01N 7/00* (2006.01)
*F04B 41/00* (2006.01)

(52) U.S. Cl.
CPC .............. *B25F 1/00* (2013.01); *B25B 21/00* (2013.01); *B25B 27/0021* (2013.01); *F04B 41/00* (2013.01); *F04F 13/00* (2013.01); *G01N 7/00* (2013.01)

(58) Field of Classification Search
CPC ..... B25B 21/00; B25B 21/02; B25B 27/0071; B25F 1/00; B25F 1/02; B25F 5/029
See application file for complete search history.

(56) References Cited

U.S. PATENT DOCUMENTS

| 2,758,081 A * | 8/1956 | Iknayan | ................. B60C 29/04 |
| | | | 137/223 |
| 4,442,738 A | 4/1984 | Spencer | |
| 5,265,504 A | 11/1993 | Fruhm | |
| 5,624,013 A * | 4/1997 | Tsai | ........................ B25F 5/001 |
| | | | 188/82.2 |

(Continued)

FOREIGN PATENT DOCUMENTS

CN    2795814 Y    7/2006
CN    202631180 U   12/2012

(Continued)

OTHER PUBLICATIONS

Taiwan Patent Office "Office Action" dated May 13, 2016, Taiwan.

(Continued)

*Primary Examiner* — Tyrone V Hall, Jr.
(74) *Attorney, Agent, or Firm* — WPAT, PC

(57) ABSTRACT

The present disclosure provides a portable power tool. The power tool includes a tool body, a tool assembly and a gas pressure detection assembly. The tool assembly includes a tool bit furnished detachably in an end of the tool body. The gas pressure detection assembly is furnished detachably in another end of the tool body. The gas pressure detection assembly is communicatively coupled to the tool body.

20 Claims, 7 Drawing Sheets

(56) References Cited

U.S. PATENT DOCUMENTS

| | | | |
|---|---|---|---|
| 5,788,021 A * | 8/1998 | Tsai | B25B 21/00 188/67 |
| 5,883,306 A | 3/1999 | Hwang | |
| 5,904,080 A | 5/1999 | Anderson et al. | |
| 5,984,022 A * | 11/1999 | Harman, Jr. | B25F 5/001 173/176 |
| 6,006,385 A | 12/1999 | Kershaw et al. | |
| 6,273,582 B1 | 8/2001 | Taggart et al. | |
| 6,286,397 B1 | 9/2001 | Taggart et al. | |
| 6,488,451 B1 * | 12/2002 | Hartman | B25F 5/001 408/124 |
| 6,826,951 B1 | 12/2004 | Schuessler, Jr. et al. | |
| 7,258,046 B2 | 8/2007 | Fruhm et al. | |
| 7,306,366 B1 | 12/2007 | Camenzind et al. | |
| 8,806,991 B2 | 8/2014 | Grand | |
| 9,028,088 B2 | 5/2015 | Vanko et al. | |
| 9,095,966 B2 * | 8/2015 | Hsieh | B60C 23/0496 |
| 2004/0107938 A1 | 6/2004 | Everts et al. | |
| 2006/0071765 A1 | 4/2006 | Lin | |
| 2006/0104732 A1 * | 5/2006 | Huang | B25F 5/021 408/124 |
| 2006/0156859 A1 * | 7/2006 | Nemetz | B25D 16/00 74/606 R |
| 2009/0107229 A1 * | 4/2009 | Bucknell | B25B 27/0057 73/146.8 |
| 2011/0216528 A1 | 9/2011 | Hung | |
| 2014/0008093 A1 * | 1/2014 | Patel | H02J 7/00 173/217 |
| 2015/0165602 A1 * | 6/2015 | Seith | B25F 5/029 173/46 |

FOREIGN PATENT DOCUMENTS

| | | |
|---|---|---|
| CN | 203542555 U | 4/2014 |
| TW | 342091 | 10/1998 |
| TW | 352654 | 2/1999 |
| TW | 386479 | 4/2000 |
| TW | 403020 | 8/2000 |
| TW | 479002 | 3/2002 |
| TW | 579922 | 3/2004 |
| TW | 580272 | 3/2004 |
| TW | M265248 | 5/2005 |
| TW | M291902 | 6/2006 |
| TW | M293856 | 7/2006 |
| TW | I273002 | 2/2007 |
| TW | M375584 | 3/2010 |
| TW | 2013032969 A | 9/2010 |
| TW | I332559 | 11/2010 |
| TW | M441554 | 11/2012 |
| TW | 201341128 A | 10/2013 |
| TW | M491560 | 12/2014 |
| TW | M501333 | 5/2015 |
| TW | I501847 | 10/2015 |

OTHER PUBLICATIONS

R E Anakwe, J S Huntley, and Jane E McEachan, "Grip Strength and Forearm Circumference in a Healthy Population", Nov. 3, 2005, Journal of Hand Surgery, Queen Margaret University, Edinburgh, Scotland, United Kingdom.

I. Sasada, Y. Etoh, and K. Kato, "A Figure-of-Eight Flexible Pickup Coil for a Magnetostrictive Torque Sensor", Oct. 2006, p. 3309-3311, vol. 42, IEEE Transactions on Magnetics, Department of Applied Science for Electronics and Materials, Kyushu University Fukuoka 816-8580, Japan.

Qiaokang Liang, Dan Zhang, Yunjian Ge, and Quanjun Song, "A Novel Miniature Four-Dmensional Force/Torque Sensor With Overload Protection Mechanism", Dec. 2009, p. 1741-1747, vol. 9, No. 12, IEEE Sensors Journal.

Takeo Ishikawa, Kazutoshi Takahashi, Quang Viet Ho, Michio Matsunami, and Nobuyuki Kurita, "Analysis of Novel Brushless DC Motors Made of Soft Magnetic Composite Core", Feb. 2012, p. 971-974, vol. 48, No. 2, IEEE Transactions on Magnetics, Gunma University, 1-5-1 Tenjin-cho, Kiryu, Gunma, 376-8515, Japan.

Noaman Makki and Remon Pop-Iliev, "Battery-and wire-less tire pressure measurement systems (TPMS) sensor", Mar. 30, 2012, Springer-Verlag.

* cited by examiner

PORTABLE POWER TOOL

CROSS REFERENCE TO RELATED APPLICATION

This application also claims priority to Taiwan Patent Application No. 104135254 filed in the Taiwan Patent Office on Oct. 27, 2015 the entire content of which is incorporated herein by reference.

TECHNICAL FIELD

The present disclosure relates to a portable power tool, and more particularly, to a multifunction portable power tool.

BACKGROUND

Conventionally, portable power tools are commonly used in jobs like home improvement and carpenter works. Thus, their designs are generally function-oriented with higher torque and higher rotation speed in mind. However, for achieving higher torque and higher rotation speed, the inevitable consequence may be the heavier and bulkier body structure and ease to produce sharp noise in operation. Not to mention that the manufacturing cost of such high-torque high-speed power tools may be increased. In short, despite the design of a conventional portable power tool is always very function-oriented, it may be still not appearing to users since it can be too pricey and too bulky.

In addition, generally the aforesaid portable power tools are not user friendly especially in a condition when it is not being used. It is noted that users usually stores their unused portable power tools in their tool cabinets or tool boxes, and since such portable power tools are generally single-function devices that they are not capable of performing functions they are not designed to do, it is possible for a users to carry a plurality of such portable power tools of different functions in their tool boxes just for responding to the actual needs on site. This will not only cause heavy burden to the users, but also is not convenient in usage.

SUMMARY

The present disclosure relates to a multifunction portable power tool that can be transformed between various function modes to be used in different tasks as required, and thereby not only the usage convenience is increased, but also the load for carrying the power tool around can be relieved.

The present disclosure provides a portable power tool, which comprises: a frame, a tool assembly and a gas pressure detection assembly. The tool assembly is furnished detachably in an end of the frame. The gas pressure detection assembly is furnished detachably in another end of the frame while being electrically coupled to the frame.

By the cooperative between the tool assembly and a gas pressure detection assembly, the portable power tool is a multifunction tool that is able to operate as a power tool or as a common manual tool, while it is also capable of working as a tire pressure detector or as an air pump. Since the portable power tool of the present disclosure can be transformed between various function modes so as to be used in different tasks as required, it is convenience to be used in almost any location for any tasks.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
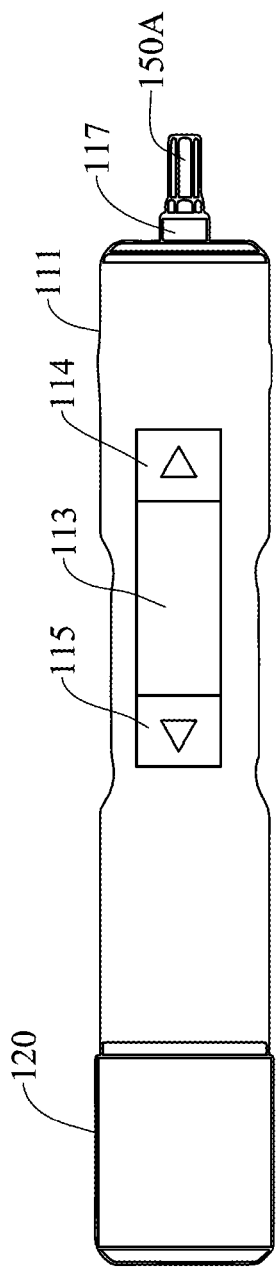
FIG. 1 is a schematic view of a portable power tool of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
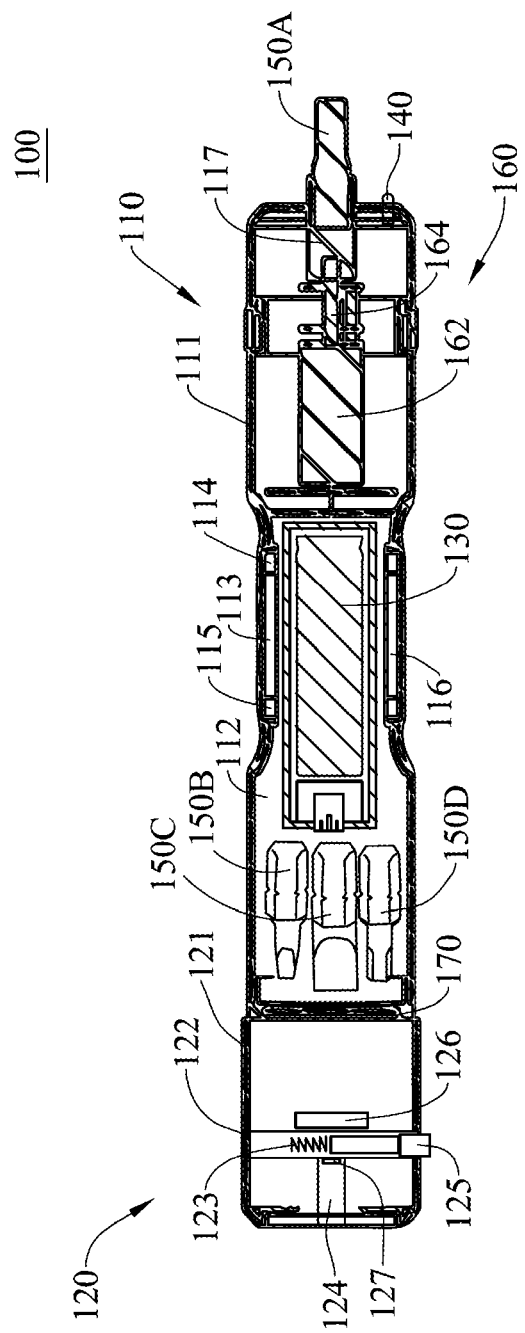
FIG. 2 is a schematic diagram showing the interior design of a portable power tool according to an embodiment of the present disclosure.
Figure 3:
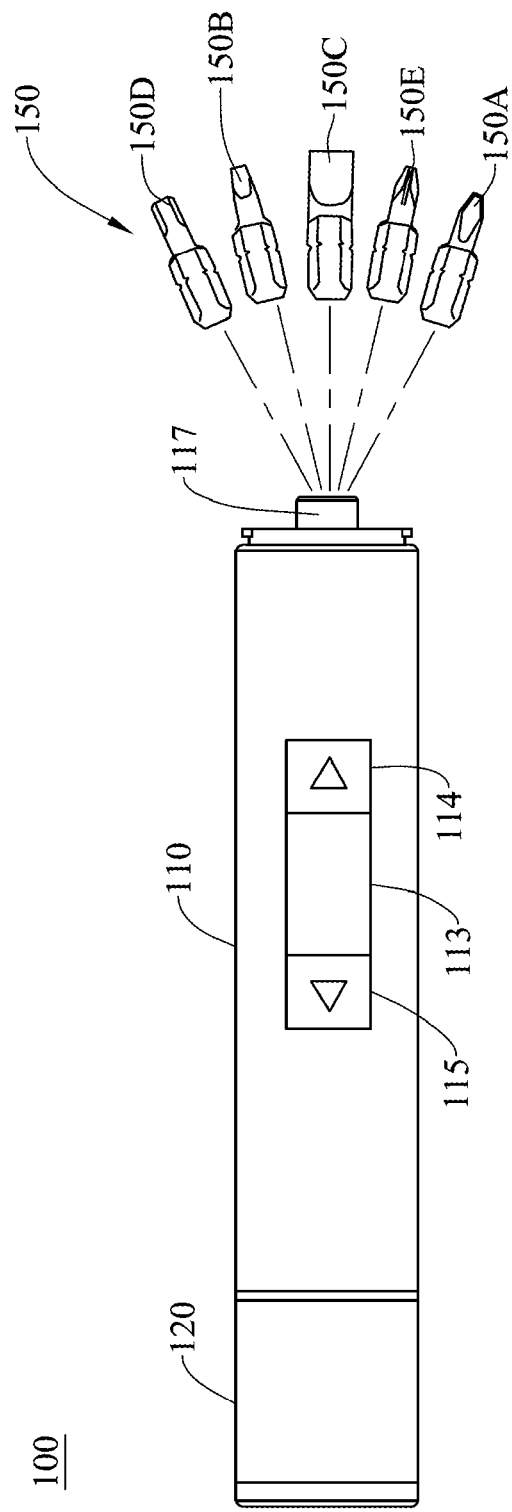
FIG. 3 is a schematic diagram showing a portable power tool with multiple tools for selection according to the present disclosure.
Figure 4:
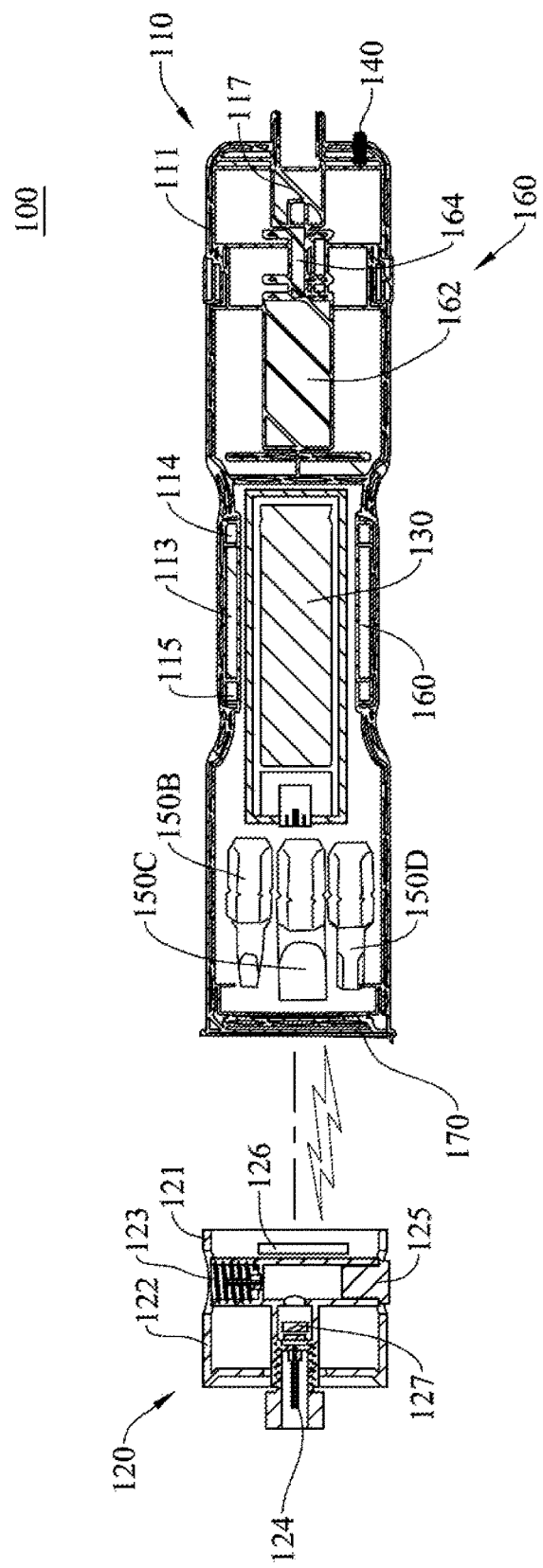
FIG. 4 is a schematic diagram showing the portable power tool of FIG. 2 that is ready to work with one selected tool.
Figure 5:
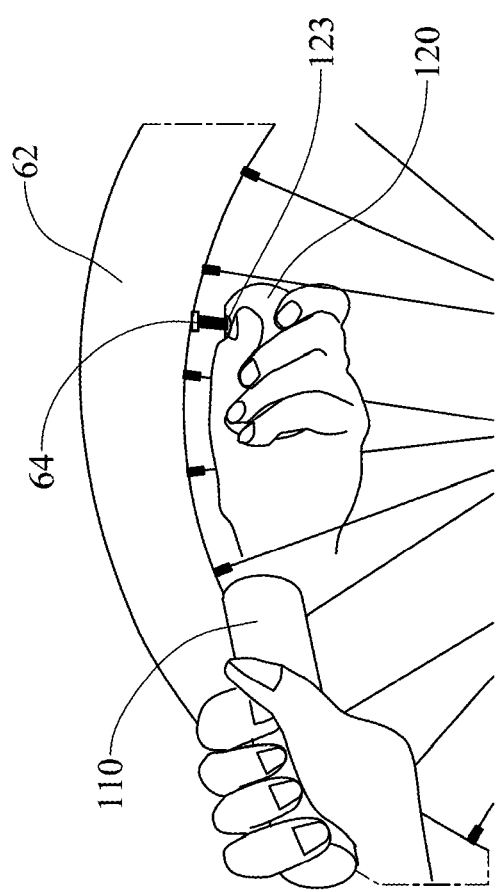
FIG. 5 is a schematic diagram showing a portable power tool of the present disclosure that is being used as a tire pressure detector.
Figure 6:
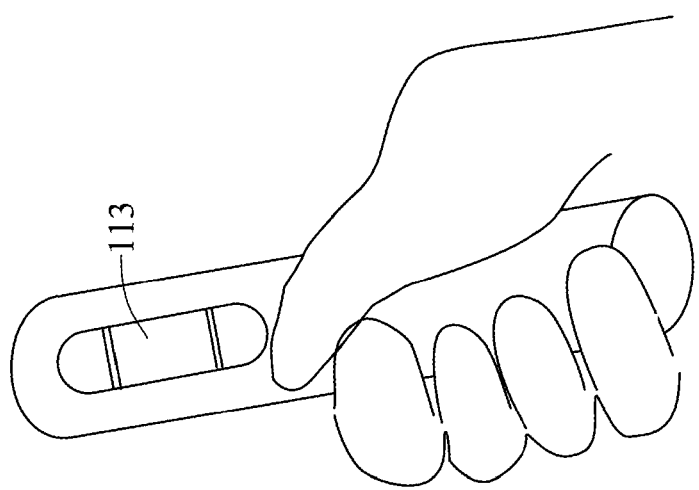
FIG. 6 is a schematic diagram showing how tire pressures can be displayed on a portable power tool of the present disclosure.
Figure 7:
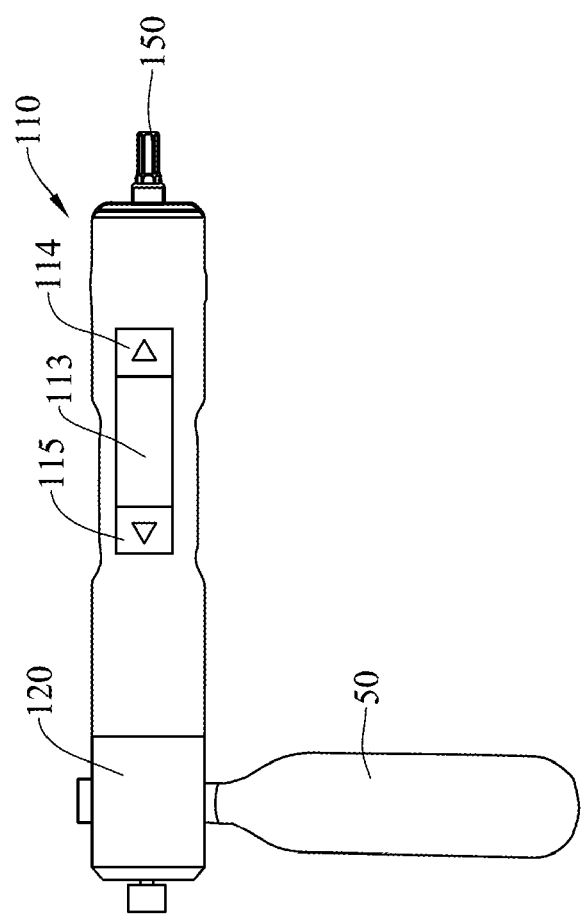
FIG. 7 is a schematic diagram showing a portable power tool of the present disclosure that is being used as an air pump.

FIG. 1 is a schematic view of a portable power tool of the present disclosure. FIG. 2 is a schematic diagram showing the interior design of a portable power tool according to an embodiment of the present disclosure. FIG. 3 is a schematic diagram showing a portable power tool with multiple tools for selection according to the present disclosure. FIG. 4 is a schematic diagram showing the portable power tool of FIG. 2 that is ready to work with one selected tool. FIG. 5 is a schematic diagram showing a portable power tool of the present disclosure that is being used as a tire pressure detector. FIG. 6 is a schematic diagram showing how tire pressures can be displayed on a portable power tool of the present disclosure. FIG. 7 is a schematic diagram showing a portable power tool of the present disclosure that is being used as an air pump.

In an embodiment shown in FIG. 1 to FIG. 4, a portable power tool 100 comprises: a frame 110, a gas pressure detection assembly 120 and a tool assembly 150, in which the tool assembly 150 is furnished detachably in an end of the frame 110, and the gas pressure detection assembly 120 is furnished detachably in another end of the frame 110 while being electrically coupled to the frame 110.

It is noted that the frame 110 can be made of a metal, a plastic, a composite material or an organic material whereas the metal can be an aluminum alloy, iron, stainless steel or cast iron; the plastic can be ABS, PC, PP, or PS; the composite material can be a carbon fiber or a glass fiber; and the organic material can be wool or bamboo.

In this embodiment, the frame 110 is further comprising: a case 111, a containing space 112, a display element 113, a first control element 114, a second control element 115, a third control element 116, a tool coupler 117, a first energy storage element 130, a lighting element 140 and a power transmission assembly 160.

The containing space 112 is a space formed and enclosed inside the case to be used for storing uncoupled bits compatible with the tool assembly 150.

As shown in FIG. 3, the tool assembly 150 includes at least one bit 150A~150E, whereas the at least one bit 150A~150E can be a slotted screwdriver bit, a crosshead screwdriver bit, a hex key wrench, or a star key wrench, but it is not limited thereby.

In an embodiment, a bit 150A selected from bits compatible with the tool assembly 150, as shown in FIG. 2, is coupled to one end of the frame 110 for allowing the bit 150A to connected to the power transmission assembly 160, while enabling the rest of the compatible bits, such as the bits 150B~150D that are shown in FIG. 2 to be stored in the containing space 112. Obviously the embodiment shown in FIG. 2 is only for illustration and the present disclosure is not limited thereby, so that it can be the bit 150B to be selected while allowing the bit 150A along with the rest of the bits 150C and 150D to be stored in the containing space 112. It is noted that although there are only bits 150B~150D that are stored in the containing space 112 in FIG. 2, the present disclosure is not limited thereby, since the portable power tool of the present disclosure can be formed with an containing space of any size at will to be used for storing any amount of bits as required.

Thus, there can be more than one types of bits 150A~150E to be used in the present disclosure, as shown in FIG. 3, that can be selected by a user for a variety of working conditions. In FIG. 2, the bit 150A is selected and inset into the tool coupler 117 to be coupled to the power transmission assembly 160, while the rest of the bits 150B~150E are stored in the containing space 112.

The power transmission assembly 160 that is furnished inside the case 110 is composed of a motor 162 and a reducer 164 in a manner that the motor 162 is coupled to the reducer 164 while enabling the reducer 164 to be coupled to one bit selected from the bits 150A~150E. It is noted that although in this embodiment the portable power tool 100 is configured with a reducer, the reducer is not necessary and the portable power tool of the present disclosure can do well without the reducer as the overall volume can be decreased without the reducer and also the manufacturing cost is reduced.

The first energy storage element 130 is furnished inside the case 111 at a position between the containing space 112 and the power transmission assembly 160. The first energy storage element 130 can be a power supply such as a lithium battery set or a nickel-cadmium battery set; and further the first energy storage element 130 can includes a rechargeable battery that can be adapted to connect to an USB device externally for charging.

By the power from the first energy storage element 130, the power transmission assembly 160 can be driven to rotate for bringing along the tool assembly 150 to rotate accordingly, as the selected bit 150A in FIG. 2, so that the present disclosure is appeared to be a portable power tool. On the other hand, when the power is turned off and there is no power for the power transmission assembly 160, the gear set in the reducer 164 is locked for fixing the bit in the tool assembly 150 from rotation, so that the portable power tool of the present disclosure can be used as a manual tool.

The lighting element 140 is furnished at the front end of the frame 110 next to the tool assembly 150. In this embodiment, the lighting element 140 is a device selected from the group consisting of: a light emitting diode (LED) device, a tungsten lamp, and a halogen lamp.

The display element 113, the first control element 114, the second control element 115 and the third control element 116 are furnished respectively on the surface of the case 111 of the frame 110, in which the display element 113 and the third control element 116 are furnished respectively on two opposite sides of the case 111, while allowing the display element 113 to be furnished at a side of the first control element 114 and the second control element 115. It is noted that the relative positioning of the display element 113, the first control element 114 and the second control element 115 that are shown in FIG. 1 is only for illustration and thus the present disclosure is not limited thereby.

The first control element 114 and the second control element 115 are used to activate the power transmission assembly 160 to rotate and thus to drive the tool assembly 150 to rotate clockwise or counterclockwise. The third control element 116 is used for turning the lighting element 140 on or off.

As shown in FIG. 1 and FIG. 2, a user is able to activate the power transmission assembly 160 by pressing either the first control element 114 or the second control element 115, by that the bit 150A can be brought along to rotate with the rotation of the power transmission assembly 160 either clockwise or counterclockwise. It is noted that the bit 150A can be replaced by any other bits selected from the bits 150B~150D at any time if required.

On the other hand, when the power is turned off on the power transmission assembly 160, the gear set in the reducer 164 is locked for fixing the bit in the tool assembly 150 from rotation, such as the bit 150A shown in FIG. 2, so that portable power tool of the present disclosure can be used as a manual tool. As the power can be turned on or off by the user, the portable power tool of the present disclosure is able to function as a manual tool or power tool at will.

Furthermore, in a condition when extra lighting is required, the user can simply press the third control element 116 for turning on the lighting element 140 to project a beam onto the workpiece.

The gas pressure detection assembly 120 is designed to send a detection data to the display element 113 for displaying in a wireless manner. It is noted that the display element 113 can be an LCD device, an OLED device, a TFT device or a mechanical display device, but it is not limited thereby.

The gas pressure detection assembly 120 is fixed to the frame 110 by a coupling element 170. There is no limit to the type of coupling element 170 that can be used in the present disclosure. In an embodiment, the gas pressure detection assembly 120 is screwed to the frame 110, while the screwing of the coupling element 170 can be released simply by pressing a button for detaching the gas pressure detection assembly 120 from the frame 110. In another embodiment, the frame is further being configured with a magnetic element while the gas pressure detection assembly 120 is correspondingly configured with another magnetic element, thus the gas pressure detection assembly 120 can be fixed to the frame 110 by the attracting between the two magnetic elements. Moreover, by the attracting between the two magnetic elements, the gas pressure detection assembly 120 is attracted to a specific position on the frame 110 where it is designed to be fixed to.

As shown in FIG. 4, the gas pressure detection assembly 120 includes: a shell composed of a first shell 121 and a second shell 122, a gas inlet element 123, a gas nozzle 124, a gas control element 125, a second energy storage element 126 and a gas pressure detector 127.

The shell including the first shell 121 and the second shell 122 can be made of a metal, a plastic, a composite material or an organic material whereas the metal can be an aluminum alloy, iron, stainless steel or cast iron; the plastic can be ABS, PC, PP, or PS; the composite material can be a carbon fiber or a glass fiber; and the organic material can be wool or bamboo.

The gas pressure detection assembly 120 is furnished inside the shell. In this embodiment, the gas pressure detection assembly 120 includes a device selected from the group consisting of: an electronic pressure sensor chip and a mechanic pressure sensor device, but is not limited thereby.

The gas nozzle 124 which can be made of a metal or a plastic is connected to one end of the gas pressure detector 127, whereas another end of the gas pressure detector 127 is connected to the gas control element 125.

In this embodiment, the gas control element 125 is furnished spacing from the gas inlet element 123 by a distance. Moreover, the gas control element 125 can be a control valve, and the gas inlet element 123 can be made of a metal, a plastic, or a composite material, whereas the metal can be an aluminum alloy, iron, stainless steel or cast iron; the plastic can be ABS, PC, PP, or PS; the composite material can be a carbon fiber or a glass fiber.

The gas inlet element 123 is connected to a gas supply 50 by one end thereof, as shown in FIG. 7, whereas the gas supply 50 can be a $CO_2$ cylinder. Moreover, the gas control element 125 can be used for adjusting the distance between the gas inlet element 124 and the gas control element 125, and thereby, the amount of gas inlet can be controlled accordingly. In another embodiment, the gas supply 50 can be an air pump, but is not limited thereby.

The second energy element 126 is furnished inside the first shell 121 of the shell, whereas the second energy element 126 can be a lithium battery set or a nickel-cadmium battery set, and the likes, whichever is capable of providing power to the gas pressure detector 127.

In view of the frame 110, the first energy storage element 130 that is furnished inside the frame 110 can be used as a portable power source by itself.

As shown in FIG. 5, by insetting a tire valve 64 of a bicycle tire 62 into the gas inlet element 123, the gas inlet element 123 is able to inflate the tire 62. Moreover, by connecting the gas nozzle 124 to a tire, the pressure of the tire can be checked, whereas the gas pressure detector 127 is designed to send a detection data to the display element 113 for displaying in a wireless manner, as shown in FIG. 6.

As shown in FIG. 7, the gas supply 50 is connected to the gas inlet element 124 for inflating a tire. However, although the gas pressure detection assembly 120 is integrated with the frame 110, the gas pressure detection assembly 120 is able to work independently with the gas supply 50.

To sum up, by the cooperation between the tool assembly and a gas pressure detection assembly, the portable power tool is a multifunction tool that is able to operate as a power tool or as a common manual tool, while it is also capable of working as a tire pressure detector or as an air pump. Since the portable power tool of the present disclosure can be transformed between various function modes so as to be used in different tasks as required, it is conveniently used in almost any location for any tasks.

In addition, as the bit in the present disclosure can be locked from rotating by the use of a locking element, the portable power tool is able to function as a manual tool, so that the portable power tool of the present disclosure is able to function as a manual tool or power tool at will.

In the aforesaid description, the gas pressure detection assembly 120 can be integrated with the frame 110 so as to work cooperatively, or the gas pressure detection assembly 120 is able to work independently while separating from the frame 110. In view of the frame 110, since the first energy storage element 130 is furnished inside the frame 110, the frame 110 can be used as a portable power source by itself.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A portable power tool, comprising:
    a frame disposed at one distal end of the portable power tool, the frame internally housing a power transmission assembly comprising a motor and a reducer;
    a tool assembly including a single bit detachably disposed at a distal end of the frame, the single bit coupled to the reducer; and
    a gas pressure detection assembly detachably disposed at the other distal end of the portable power tool opposite the single bit, the gas pressure detection assembly communicatively coupled to the frame;
    wherein, a gear set in the reducer is locked and unable to rotate while the power transmission assembly is unpowered.

2. The portable power tool of claim 1, the frame further internally housing a case and a containing space;
    wherein, the power transmission assembly and the containing space are respectively disposed in an interior of the case;
    wherein, one or more additional bits compatible with the reducer are stored in the containing space.

3. The portable power tool of claim 2, wherein the frame further comprising:
    a first energy storage element, furnished inside the case at a position between the power transmission assembly and the containing space, the first energy storage element transmitting electricity to the power transmission assembly.

4. The portable power tool of claim 3, wherein the first energy storage element is a rechargeable battery.

5. The portable power tool of claim 3, wherein the first energy storage element receives power from an USB device when externally connected thereto.

6. The portable power tool of claim 2, further comprising:
    a first control element; and
    a second control element;
    wherein, the first control element and the second control element are furnished respectively on the exterior of the frame for enabling the first control element and the second control element to activate the power transmission assembly to rotate accordingly and thus to drive the tool assembly to rotate clockwise or counterclockwise, respectively.

7. The portable power tool of claim 6, further comprising:
a display element, furnished on the frame proximal to the first control element and the second control element;
wherein the display element receives a detection data from the gas pressure detection assembly and displays the detection data on the display element.

8. The portable power tool of claim 7, further comprising:
a lighting element, furnished on the frame at a position next to the tool assembly; and
a third control element, furnished on the frame, for turning the lighting element on or off.

9. The portable power tool of claim 8, wherein the lighting element is a device selected from the group consisting of: a light emitting diode (LED) device, a tungsten lamp, and a halogen lamp.

10. The portable power tool of claim 2, wherein the single bit is a bit selected from the group consisting of: a slotted screwdriver bit, a crosshead screwdriver bit, a hex key wrench, and a star key wrench.

11. The portable power tool of claim 2, wherein the motor is coupled to the reducer while the reducer is coupled to the single bit.

12. The portable power tool of claim 2, wherein the frame is made of a material selected from the group consisting of: a metal, a plastic, a composite material and an organic material.

13. The portable power tool of claim 1, wherein the gas pressure detection assembly is fixed to the frame by a coupling element.

14. The portable power tool of claim 1, wherein the gas pressure detection assembly further comprising:
a shell;
a gas pressure detector, furnished inside the shell;
a gas nozzle, connected to an end of the gas pressure detector;
a gas inlet element; and
a gas control element, connected to an end of the gas pressure detector such that the gas control element is spaced from the gas inlet element by a distance.

15. The portable power tool of claim 14, wherein the gas pressure detector is a device selected from the group consisting of: an electronic pressure sensor chip and a mechanic pressure sensor device.

16. The portable power tool of claim 14, wherein the gas inlet element is connected to a gas supply by one end and the gas control element controls the amount of gas passing through the gas inlet element.

17. The portable power tool of claim 14, wherein the gas inlet element is made of a material selected from the group consisting of: an aluminum alloy, iron, stainless steel and galvanized iron.

18. The portable power tool of claim 14, wherein the shell is made of a material selected from the group consisting of: a metal, a plastic, and a composite material.

19. The portable power tool of claim 18, wherein the metal can be an aluminum alloy, iron, stainless steel, or cast iron; and the plastic can be ABS, PC, PP or PS.

20. The portable power tool of claim 14, wherein the gas pressure detection assembly further comprising:
a second energy storage element, furnished inside the shell for providing power to the gas pressure detector.

* * * * *